United States Patent [19]
Chen et al.

[11] Patent Number: 6,160,134
[45] Date of Patent: Dec. 12, 2000

[54] PROCESS FOR PREPARING CHIRAL CYCLOPROPANE CARBOXYLIC ACIDS AND ACYL GUANIDINES

[75] Inventors: Bang-Chi Chen, Plainsboro, N.J.; Joseph E. Sundeen, Yardley, Pa.; Jeffrey T. North, Syracuse, N.Y.; Annie J. Pullockaran, Trenton, N.J.; Saleem Ahmad, Wall, N.J.; Shung C. Wu, Princeton, N.J.; Karnail S. Atwal, Newtown, Pa.; Sundeep Dugar, Bridgewater, N.J.

[73] Assignee: Bristol-Myers Squibb co., Princeton, N.J.

[21] Appl. No.: 09/329,472

[22] Filed: Jun. 10, 1999

Related U.S. Application Data

[63] Continuation-in-part of application No. 09/198,159, Nov. 23, 1998.
[60] Provisional application No. 60/068,790, Dec. 24, 1997, and provisional application No. 60/073,740, Feb. 5, 1998.
[51] Int. Cl.[7] ............... C07D 307/87; C07D 307/79; C07D 307/80; C07C 61/04; C07C 49/293
[52] U.S. Cl. ............... 549/462; 546/332; 548/125; 548/341.5; 548/376.1; 549/467; 549/471; 549/78; 549/385; 549/398; 562/401; 562/506
[58] Field of Search ................ 549/462, 471, 549/78, 398, 385, 467; 562/401, 506; 546/332; 548/341.5, 125, 376.1

[56] References Cited

U.S. PATENT DOCUMENTS

| | | | |
|---|---|---|---|
| 4,542,235 | 9/1985 | Minai | 562/401 |
| 4,681,952 | 7/1987 | Lantzsch | 549/61 |
| 5,336,689 | 8/1994 | Weber et al. | |
| 5,756,535 | 5/1998 | Schwark et al. | |

FOREIGN PATENT DOCUMENTS

| | | |
|---|---|---|
| 0639573A1 | 2/1995 | European Pat. Off. |
| 0738712A1 | 10/1996 | European Pat. Off. |
| 744397A2 | 11/1996 | European Pat. Off. |
| 790245A1 | 8/1997 | European Pat. Off. |
| 0803501A1 | 10/1997 | European Pat. Off. |
| 959245 | 4/1997 | Japan |
| 967340 | 11/1997 | Japan |
| 1437832 | 6/1976 | United Kingdom |
| WO97/46226 | 11/1997 | WIPO |
| WO 98/25606 | 6/1998 | WIPO |

OTHER PUBLICATIONS

March J. Advanced Organic Chemistry. Second edition. P. 73, 1977.

Falmagne, J–B. et al, "Cyclobutanone and Cyclobutenone Derivatives by Reaction of Tertiary Amides with Alkens or Alkynes" Agnew. Chem. Int. Ed. Engl. 20 (1981) No. 10.

Houge, C. et al, "Models for Asymmetric [2+2]Cycloadditions" J. Am. Chem. Soc., 1982, 104, 2921–2923.

Schmit, C. et al, "A General Synthesis of Cyclobutanones from Olefins and Tertiary Amies: 3–Hexylcyclobutanone" Org. Synth. 1990, 60, 199.

*Primary Examiner*—Evelyn Mei Huang
*Attorney, Agent, or Firm*—Burton Rodney; Ronald S. Hermenau

[57] ABSTRACT

A process is provided for preparing chiral cyclopropane carboxylic acids, preferably of the structure

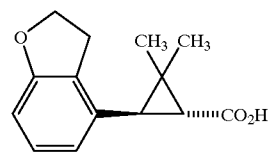

which are intermediates used in preparing acyl guanidine sodium/proton exchange (NHE) inhibitors.

15 Claims, No Drawings

PROCESS FOR PREPARING CHIRAL CYCLOPROPANE CARBOXYLIC ACIDS AND ACYL GUANIDINES

REFERENCE TO OTHER APPLICATIONS

This is a continuation-in-part of U.S. application Ser. No. 09/198,159 filed Nov. 23, 1998 which claims the benefit of provisional applications 60/068,790, filed on Dec. 24, 1997 and 60/073,740, filed on Feb. 5, 1998.

FIELD OF THE INVENTION

The present invention relates to a novel process for the preparation of chiral cyclopropane carboxylates which are key intermediates in the synthesis of sodium/proton exchange (NHE) inhibitors and melatonergic agents, and to a process for preparing acyl guanidines employing such intermediates.

BACKGROUND OF THE INVENTION 2-(2',3'-Dihydrobenzofuran-4'-yl)cyclopropane carboxylate derivatives have been prepared via cyclopropylation of 3-(2',3'-dihydrobenzofuran-4'-yl)propenoic esters or amides using hazardous reagents such as diazomethane (Catt, J. D.; Johnson, G.; Keavy, D. J.; Mattson, R. J.: Parker, M. F.; Takaki, K. S.; Yevich, J. P. WO 98/25606, Jun. 18, 1998).

A more convenient method for the preparation of simple 2-arylcyclopropane carboxylates involves the α-bromination of 3-simple aryl substituted cyclobutanone with bromine followed by ring contraction of the resulting α-bromocyclobutanone (Lantzsch, R.; Arlt, D.; Jautelat, M. U.S. Pat. No. 4,681,952, Jul. 21, 1987). However, reaction of 2,2-dimethyl-3-(2',3'-dihydrobenzofuran-4'-yl)cyclobutanone with bromine followed by ring contraction under these reaction conditions does not give the desired product without undesirable side products. Fusing a dihydrofuran ring to the phenyl group not only activates the phenyl ring for electrophilic aromatic bromination, but also provides more reactive benzylic and etheral sites for bromination compared to the desired reaction at the α-position adjacent to the ketone group. In the present invention, as will be seen, an enolate is preformed before bromination to overcome all the above mentioned side reactions, providing the desired 2-(2',3'-dihydrobenzofuran-4'-yl)cyclopropane carboxylates in high yield without costly chromatographic separation of products.

Several methods have been disclosed previously for the preparation of 3-aryl cyclobutanones (Lantzsche, R.; Arlt, D.; Janutelat, M. U.S. Pat. No. 4,681,952, Jul. 21, 1987, and Falmagne, J.-B.; Escudero, J.; Taleb-Sahraoui, S.; Ghosez, L. *Angew. Chem. Int. Ed. Engl.*, 1981, 20, 879), among which [2+2]-cycloaddition of styrene with a ketene precursor has its advantages (Falmagne, J.-B. et al, supra). While styrene itself has been successfully used in the [2+2]-cycloaddition under acidic conditions with elevated temperatures for the cycloaddition, it is not apparent if the dihydrofuran fused styrenes will survive under such acidic conditions with elevated temperatures. Dihydrofuran fused styrenes are expected to be more prone to acid catalyzed and heat induced polymerization than styrene.

Preparation of 3-phenylcyclobutanone with α-chloroenamine has also been reported (Houge, C.; Frisque-Hesbain, A. M.; Mockel, A.; Ghosez, L. *J. Am. Chem. Soc.*, 1982, 104, 2920.

SUMMARY OF THE INVENTION

The present invention provides an efficient process for the preparation of chiral cyclopropane carboxylates, key intermediates for the preparation of acyl guanidine NHE inhibitors and melatonergic agents. The process of the invention is short in reaction sequence, gives high overall yield and avoids the use and involvement of dangerous reagents such as diazomethane.

DESCRIPTION OF THE INVENTION

In accordance with the present invention, a process is provided for preparing chiral cyclopropane carboxylic acids, including esters and salts thereof, which are intermediates for use in preparing acylguanidine sodium/proton exchange (NHE) inhibitors which are useful as antianginal agents and in treating intermittent claudication. The process of the invention includes the steps of forming an α-halo cyclobutanone 5 having the structure

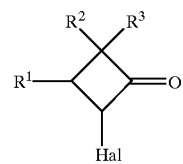

5 wherein $R^1$ is aryl or heteroaryl, $R^2$ and $R^3$ are the same or different and are each lower alkyl, or $R^2$ and $R^3$ can be joined together with the carbon to which they are attached to form a non-aromatic carbocyclic ring (namely, a cycloalkyl ring) which contains 3 to 7 ring members, preferably 5 or 6 ring members, treating the α-halo cyclobutanone with a base to form the cyclopropane carboxylic acid ester and/or salt 6, thereof of the structure

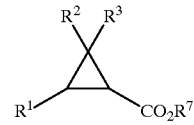

6

(where $R^7$ is H or lower alkyl)
and converting the cyclopropane carboxylic acid 6 to the corresponding chiral cyclopropane carboxylic acid 8

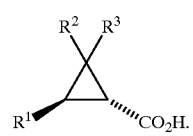

8

In accordance with the present invention, the chiral cyclopropane carboxylic acid 8 may be formed by reacting the cyclopropane carboxylic acid of the structure 6

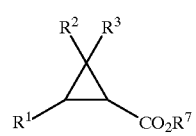

6 wherein $R^7$ is H, with a chiral amine of the structure

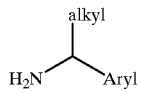

to form the cyclopropane carboxylic acid amine salt of the structure

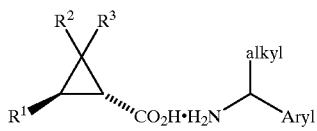

where Aryl is preferably phenyl and alkyl is preferably methyl, and treating the cyclopropane carboxylic acid amine salt 7 with aqueous acid to form the cyclopropane carboxylic acid of the structure 8.

As indicated in the compounds prepared herein, $R^2$ and $R^3$ can be taken together with the carbon to which they are attached to form a 3 to 7 membered non-aromatic carbocyclic ring which is preferably

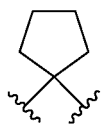

In addition, in accordance with the present invention, a process is provided for preparing the α-halo cyclobutanone 5, which process includes the steps of providing an alkylidene compound of the structure 1

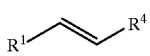

wherein $R^4$ is H or lower alkyl, reacting the alkylidene compound 1 with an N,N-disubstituted ketene iminium salt of the structure 2

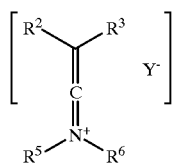

wherein $R^5$ and $R^6$ are the same or different and are each lower alkyl, and Y is trifluoromethanesulfonate (OTf), to form a cyclobutane iminium salt of the structure 3

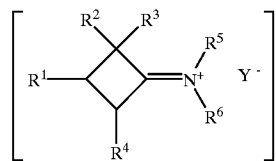

hydrolyzing the cyclobutane iminium salt 3 to form a cyclobutanone of the structure 4

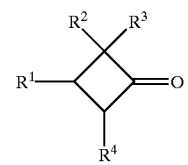

and treating the cyclobutanone 4 with a base and then a halogenating agent to form the α-halocyclobutanone of the structure 5

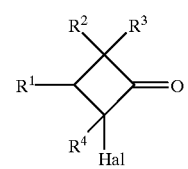

where Hal is Cl, Br, F or I.

In a preferred embodiment of the process of the invention, a chiral form of 2-(2',3'-dihydrobenzofuran-4'-yl) cyclopropane carboxylic acid of the structure 10

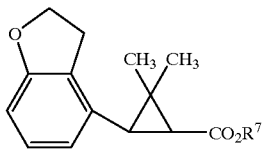

is prepared by (a) providing a 2-(2',3'-dihydrobenzofuran-4'-yl) cyclopropane carboxylic acid of the structure 10a

wherein $R^7$ is H, (b) if $R^7$ is lower alkyl, hydrolyzing the ester to the corresponding acid, (c) reacting the acid with a chiral amine of the structure 6a

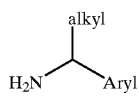

to form an amine salt of the structure 10b

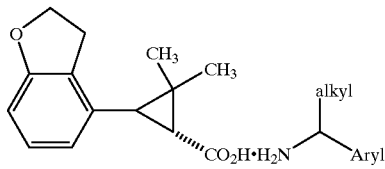

and (d) reacting the amine salt with aqueous acid to form the chiral acid of the structure 10c

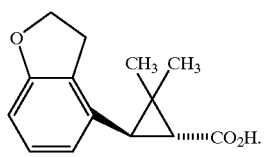

Alternatively, if in 10a

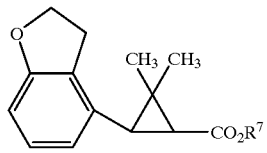

$R^7$ is lower alkyl, subjecting the above ester to enzymatic hydrolysis to form the chiral acid of the structure 10c.

The enzymatic hydrolysis may be carried out employing an esterase such as pig liver esterase.

In accordance with the present invention, the 2-(2',3'-dihydrobenzofuran-4'-yl) cyclopropane carboxylic acid or ester and/or salt thereof 10a is prepared by reacting a 4-vinyl-2,3-dihydrobenzofuran 1a

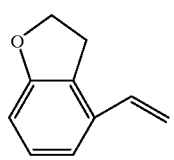

with an N,N-disubstituted ketene iminium salt of the structure 2a

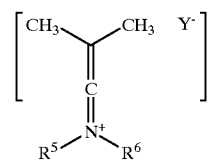

where $R^5$ and $R^6$ are the same or different and are each lower alkyl, and Y is OTf (trifluoromethanesulfonate) to form 2,2-dimethyl-3-(2',3'-dihydrofuran-4'-yl)cyclobutanone iminium salt 3a. The iminium salt is hydrolyzed to the 2,2-dimethyl-3-(2',3'-dihydrobenzofuran-4'-yl)cyclobutanone 4a

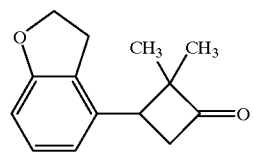

which is treated with base and halogenating agent to form the α-halocyclobutanone 5a

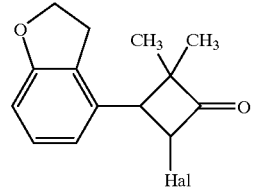

which is treated with a base to form the cyclopropane carboxylic acid compound 10a.

The alkylidene starting material 1 or 1a is known in the art and/or may be prepared employing conventional procedures such as described in the accompanying working examples.

In addition, in accordance with the present invention, a process is provided for preparing acyl guanidine sodium/proton exchange inhibitors of the structure

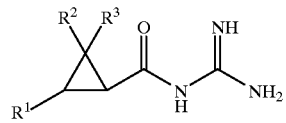

(which are disclosed in parent U.S. application Ser. No. 09/198,159), which process includes the steps of providing a chiral cyclopropane carboxylic acid of the structure 8

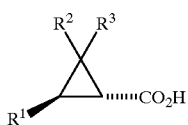

and converting the chiral cyclopropane carboxylic acid to the acyl guanide 9.

The chiral cyclopropane carboxylic acid can be converted to the acyl guanide by reacting the chiral acid 8 with guanidine in the presence of a coupling agent such as carbonyldiimidazole.

In a preferred embodiment of the invention, the chiral cyclopropane carboxylic acid 8 will have the structure 10c

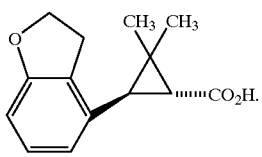

In addition, in accordance with the present invention, the following intermediates prepared by the process of the invention are novel compounds:

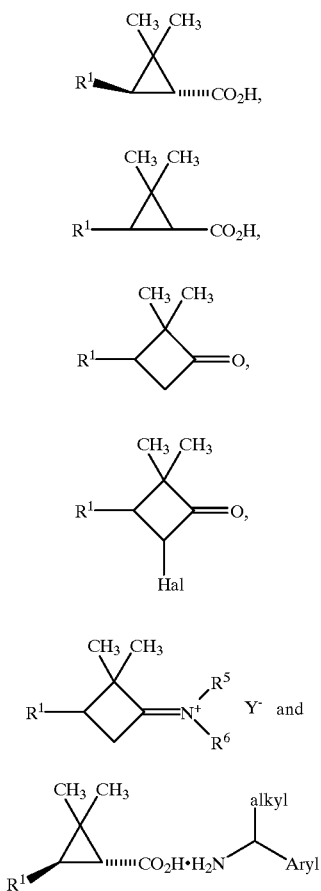

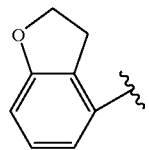

wherein $R^1$ is
$R^5$ is lower alkyl
$R^6$ is lower alkyl
and Y is OTf.

As set forth in the following Scheme I, the process of the invention for the preparation of chiral cyclopropane carboxylates involves the following chemical reactions.

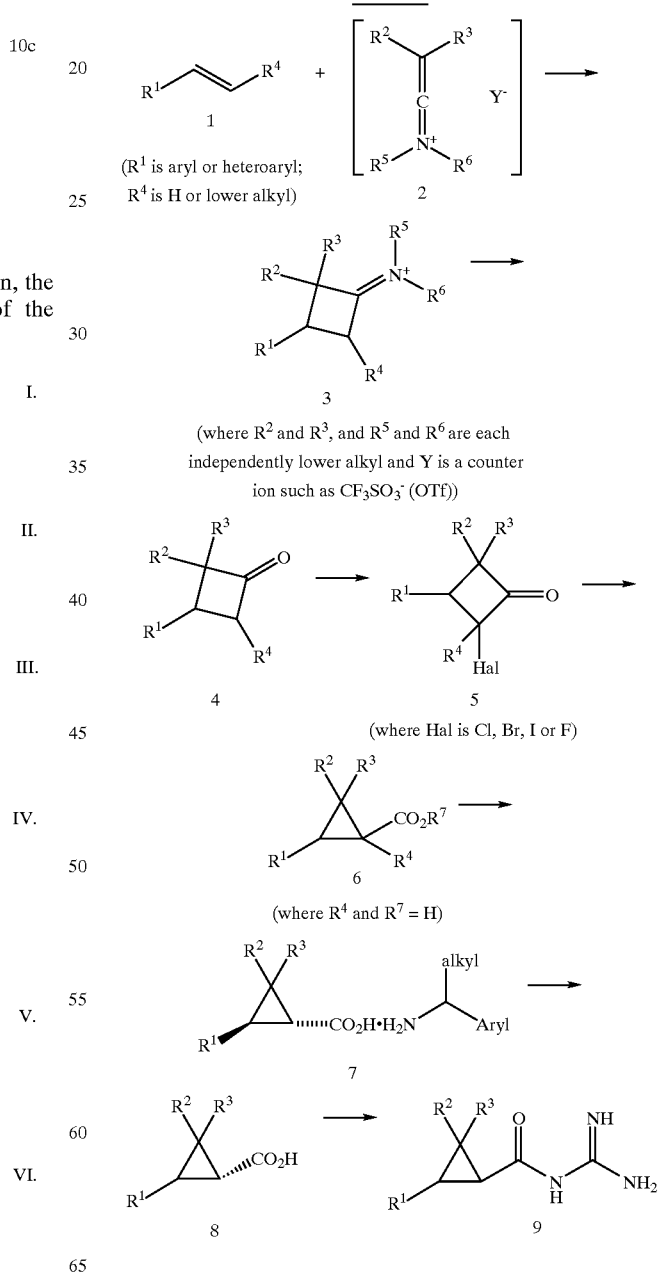

The preparation of iminium salt 3 from olefrin 1 and N,N-disubstituted ketene iminium salt 2 is carried out in a suitable solvent or solvent mixtures such as hydrocarbons, halogenated hydrocarbons, ethers, esters, ketones, amides and nitriles. The preferred solvent is dichloromethane. A molar ratio of 1:2 within the range from about 1:0.5 to about 1:5, preferably from about 1:0.8 to about 1:2, is employed.

N,N-disubstituted ketene iminium salt 2 may be generated in situ by the reaction of an N,N-disubstituted amide with an acylating reagent such as an acyl halide or anhydride in the presence of a base, such as an aromatic or aliphatic base. The preferred acylation reagent is trifluoromethanesulfonic anhydride and the preferred base is collidine.

The N,N-disubstituted ketene iminium salt 2 may alternatively be generated in situ from an α-halo-N,N-disubstituted enamine such as α-chloro-N,N-disubstituted enamine with a Lewis acid such as zinc chloride. The reaction temperatures range from 0–150° C., with 30–100° C. being preferred.

The preferred starting material 1 is 4-vinyl-2,3-dihydrobenzofuran and the preferred ketene iminium salt 2 precusors are N,N-dimethylacetamide and N,N-dimethylisobutyramide.

Cyclobutanone 4 is obtained from the corresponding iminium salt 3 by hydrolysis under aqueous conditions with the optional use of acid such as HCl or other conventional acid.

The preparation of acid 6 is carried out by generating the enolate of 4 using a base in a suitable solvent or solvent mixture followed by halogenation with a halogenating reagent to form the corresponding α-haloketone 5. The base used in this step includes LiHMDS, NaHMDS, KHMDS or any other base capable of enolyzing cyclobutanones. The preferred base is LiHMDS. A suitable solvent or solvent mixture includes ethers, hydrocarbons, or amides with the preferred solvent being THF. The temperature for the enolate formation may range from −110° to 50° C. with −80° to 25° C. being preferred. The halogenating reagent includes N-bromosuccinimide (NBS), N-chlorosuccinimide (NCS), N-iodosuccinimide (NIS), bromine, chlorine, iodine, dihalohydantoin or other electrophilic halogenating reagents with NBS being preferred.

Alternatively, the enolate may be trapped as enol ether or ester before halogenation. Moreover, the enolate or its derivative may be hydroxylated instead of halogenated to give an α-hydroxy cyclobutanone in which the α-hydroxy group may be converted to a sulfonyloxy or phosphoryloxy leaving group for the next rearrangement reaction. The hydroxylation reagent includes oxygen, bistrimethylsilylperoxide, the MoOPH reagent, the Davis' N-sulfonyloxaziridine or other electrophilic hydroxylating reagent. The α-sulfonyloxy cyclobutane may be directly prepared from the enolate or its derivative with reagents such as bissulfonylperoxide.

Treatment of the α-haloketone 5 with a base in a suitable solvent or solvent mixture forms cyclopropane carboxylic acid 6. The base used in this step includes metal hydroxide or alkyloxide or aryloxide with metal hydroxide such as sodium hydroxide being preferred. The suitable solvent or solvent mixture may be any conventional solvent with the mixture of THF and water being preferred. The reaction temperature may range from −80° to 60° C. with −20° to 40° C. being preferred.

The resolution of 6 to form 8 is carried out by reaction of 6 with an appropriate chiral amine in a suitable solvent or solvent mixture to form the corresponding amine salt 7. The chiral amine includes conventional amines for resolution purpose with (R)-1-phenylethylamine preferred. The solvent or solvent mixture includes any conventional solvent with ethanol preferred. The temperature may range from 160° to −20° C. with 80° to 0° C. preferred.

The amine salt 7 is converted to free chiral acid 8 by reaction with aqueous acid in a suitable solvent or solvent mixture. The aqueous acid includes those acids that are stronger than the carboxylic acid 6 with aqueous HCl being preferred. A suitable solvent includes any conventional solvent with ethyl acetate being preferred.

As indicated in the above reactions, it is preferred that $R^1$ is 2',3'-dihydrobenzofuran-4-yl and $R^2$ and $R^3$ are each methyl.

Acyl guanidine 9 may be prepared from the corresponding carboxylic acid 8 by using the sequence of steps outlined in Scheme II set out below. Activation of carboxylic acid 8 with various activating reagents (e.g. 1,1'-carbonyldiimidazole (CDI), thionyl chloride, oxalyl chloride, and the like) (employing a molar ratio of activating agent:acid 8 within the range from about 1:1 to about 10:1) in an organic solvent such as THF or methylene chloride, convert acids 8 to 8a. Subsequent treatment of compounds of formula 8a with guanidine in DMF or THF (employing a molar ratio of guanidine:8a within the range from about 1:1 to about 20:1) gives compounds of the formula 9.

Scheme II

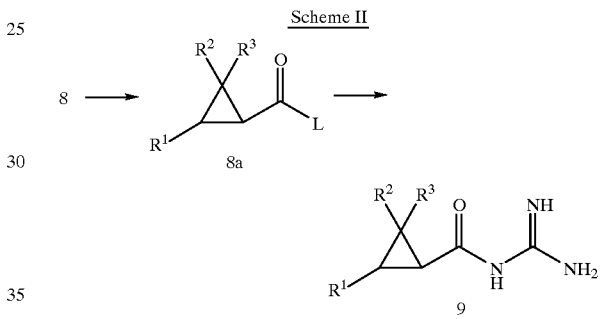

(L=a leaving group such as halide, alkoxy, aryloxy or imidazolyl).

The following definitions apply to the terms as used throughout this specification, unless otherwise limited in specific instances.

Unless otherwise indicated, the term "lower alkyl", "alkyl" or "alk" as employed herein alone or as part of another group includes both straight and branched chain hydrocarbons, containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various additional branched chain isomers thereof, and the like as well as such groups including 1 to 4 substituents which may be halogen, $CF_3$, haloalkyl, carbonyl, hydroxy, alkoxy, alkyl, aryl, cycloalkyl, alkenyl, alkenyloxy, alkynyl, alkynyloxy, alkanoyl, nitro, amino, thiol, alkythio, alkylsulfinyl, alkylsulfonyl, carboxy, alkoxycarbonyl, aminocarbonyl, alkylcarbonyloxy, alkylcarbonylamino, cycloheteroalkyl, cyano, Ar, Ar-alkyl, ArO, Ar-amino, Ar-thio, Ar-sulfinyl, Ar-sulfonyl, Ar-carbonyl, Ar-carbonyloxy or Ar-carbonylamino (wherein Ar is aryl or heteroaryl).

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, preferably 4 to 12 carbons, forming the ring and which may be fused to one aromatic ring as described for aryl, which include cyclopropyl, cyclobutyl, cyclopentyl, cyclohexyl, cycloheptyl, cyclooctyl, cylodecyl and cyclododecyl, cyclohexenyl,

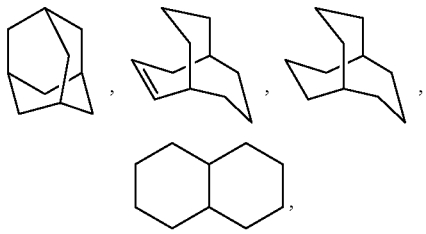

any of which groups may be optionally substituted with 1 to 4 substituents which may be any of the substituents set out herein for alkyl.

The term "aryl" as employed herein alone or as part of another group refers to monocyclic and bicyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring (such as aryl, cycloalkyl, heteroaryl or cycloheteroalkyl rings) and may be optionally substituted through available carbon atoms with 1, 2, or 3 groups selected from hydrogen, halo, haloalkyl, alkyl, haloalkyl, alkoxy, haloalkoxy, alkenyl, trifluoromethyl, trifluoromethoxy, alkynyl, cycloalkylalkyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl or any of the substituents set out herein for alkyl.

The term "amino" as employed herein alone or as part of another group may optionally be independently substituted with one or two substituents, which may be the same or different, such as alkyl, aryl, arylalkyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl or thioalkyl. These substituents may be further substituted with a carboxylic acid or any of the substituents for alkyl.

The term "lower alkylthio", alkylthio", "arylthio" or "aralkylthio" as employed herein alone or as part of another group includes any of the above alkyl, aralkyl or aryl groups linked to a sulfur atom.

The term "lower alkylamino", "alkylamino", "arylamino", or "arylalkylamino" as employed herein alone or as part of another group includes any of the above alkyl, aryl or arylalkyl groups linked to a nitrogen atom.

Unless otherwise indicated, the term "lower alkenyl", or "alkenyl" as used herein by itself or as part of another group refers to straight or branched chain radicals of 2 to 20 carbons, preferably 3 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonylamino, nitro, cyano, thiol, and/or alkylthio.

Unless otherwise indicated, the term "lower alkynyl" or "alkynyl", as used herein by itself or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio.

Where alkyl groups as defined above have single bonds for attachment to other groups at two different carbon atoms, they are termed "alkylenel" groups and may optionally be substituted as defined above for "alkyl".

Where alkenyl groups as defined above and alkynyl groups as defined above, respectively, have single bonds for attachment at two different carbon atoms, they are termed "alkenylene groups" and "alkynylene groups", respectively, and may optionally be substituted as defined above for "alkenyl" and "alkynyl".

The term "halogen" or "halo" as used herein alone or as part of another group refers to chlorine, bromine, fluorine, and iodine as well as $CF_3$, with chlorine or fluorine being preferred.

The term "metal ion" refers to alkali metal ions such as sodium, potassium or lithium and alkaline earth metal ions such as magnesium and calcium, as well as zinc and aluminum.

The term "cycloheteroalkyl" as used herein alone or as part of another group refers to a 5-, 6- or 7-membered saturated or partially unsaturated ring which includes 1 to 2 hetero atoms such as nitrogen, oxygen and/or sulfur, linked through a carbon atom or a heteroatom, where possible, optionally via the linker $(CH_2)_p$ (which is defined above), such as

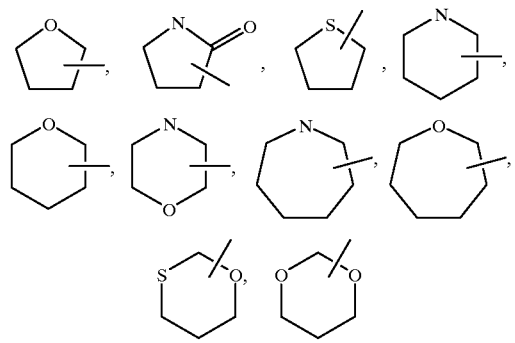

and the like. The above groups may include 1 to 4 substituents such as alkyl, halo, oxo and/or any of of the substituents for alkyl as set out herein. In addition, any of the above rings can be fused to a cycloalkyl, aryl, heteroaryl or cycloheteroalkyl ring.

The term "heteroaryl" as used herein alone or as part of another group refers to a 5- or 6-membered aromatic ring which includes 1, 2, 3 or 4 hetero atoms such as nitrogen, oxygen or sulfur, and such rings fused to an aryl, cycloalkyl, heteroaryl or cycloheteroalkyl ring (e.g. benzothiophenyl, indolyl), and includes possible N-oxides. The heteroaryl group may optionally include 1 to 4 substituents such as any of the substituents for alkyl set out above. Examples of heteroaryl groups include the following:

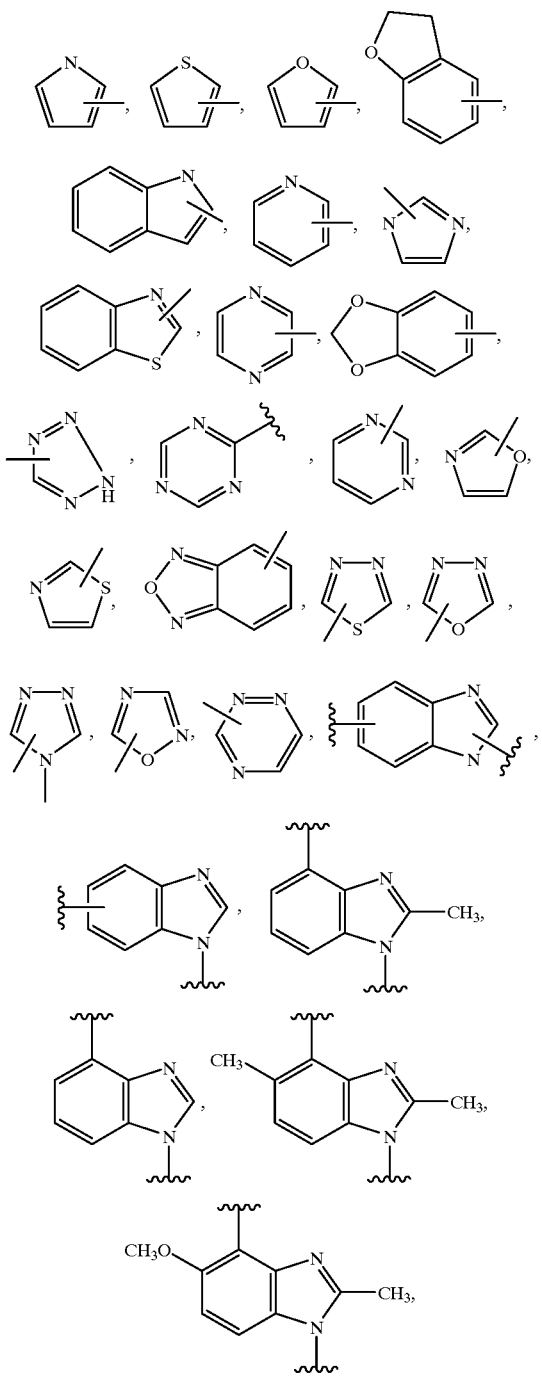

and the like.

In the case where $R^1$ is heteroaryl, $R^1$ is preferably

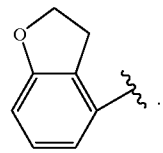

The term "cycloheteroalkylalkyl" as used herein alone or as part of another group refers to cycloheteroalkyl groups as defined above linked through a C atom or heteroatom to a $(CH_2)_p$ chain, where p is 1 to 5.

The term "heteroarylalkyl" or "heteroarylalkenyl" as used herein alone or as part of another group refers to a heteroaryl group as defined above linked through a C atom or heteroatom to a $—(CH_2)_p—$ chain, alkylene or alkenylene as defined above.

The term "polyhaloalkyl" as used herein refers to an "alkyl" group as defined above which includes from 2 to 9, preferably from 2 to 5, halo substituents, such as F or Cl, preferably F, such as $CF_3CH_2$, $CF_3$ or $CF_3CF_2CH_2$.

The term "polyhaloalkyloxy" as used herein refers to an "alkoxy" or "alkyloxy" group as defined above which includes from 2 to 9, preferably from 2 to 5, halo substituents, such as F or Cl, preferably F, such as $CF_3CH_2O$, $CF_3O$ or $CF_3CF_2CH_2O$.

The acyl guanidine compounds of formula 9 prepared by the process of the invention exhibit $Na^+/H^+$ exchange inhibitory activity, and hence, are useful for treating or preventing disorders caused by intracellular acidosis during myocardial ischemia, such as cardiac dysfunction, myocardial necrosis, arrhythmia, reperfusion injury, and the like which are observed in ischemic heart diseases (e.g., myocardial infarction and angina pectoris).

Thus, acyl guanidine compounds of formula 9 prepared by the process of the invention may be used as antiischemic agents, i.e., for the treatment of ischemic conditions such as myocardial ischemia, cerebral ischemia, peripheral vascular disease including peripheral atherosclerotic disease including intermittent claudication and lower limb ischemia. Thus, a composition containing one (or a combination) of the compounds of this invention, may be administered to a species of mammal (e.g., humans, dogs or cats) suffering from an ischemic condition.

The acyl guanidine compounds prepared by the process of the invention can be administered as a single dose, or two to four divided daily doses, provided on a basis of about 0.001 to about 100 mg per kilogram of body weight per day, preferably about 0.1 to about 25 mg per kilogram of body weight per day is appropriate. The substance is preferably administered orally, but parenteral routes such as the subcutaneous, intramuscular, intravenous or intraperitoneal routes or any other suitable delivery system, such as intranasal or transdermal routes can also be employed.

As a result of the $Na^+/H^+$ exchange inhibiting activity of the acyl guanidine compounds, these compounds are also useful in the treatment of cardiovascular disorders. For example, such compounds are useful as therapy for congestive heart failure, therapy for peripheral vascular disorders including peripheral atherosclerotic disease including intermittent claudication, as well as Raynaud's Disease and LeRiches Syndrome, therapy for hypertension, as antianginal agents, as antifibrillatory agents, and in limiting myocardial infarction.

Such acyl guanidine compounds are additionally expected to be useful in the treatment of cerebral ischemia (e.g., stroke).

As a result of the Na/H exchange inhibiting activity, the acyl guanidine compounds can also be used for the treatment of diseases associated with proliferation of smooth muscle cells, mesangial cells, and fibroblasts. Such diseases include restenosis after angioplasty, renal fibrosis, atherosclerosis, hepatic fibrosis, prostate hypertrophy, pulmonary fibrosis and glomerular nephrosclerosis.

Other uses for the acyl guanidine compounds which inhibit Na/H exchange include treatments for diseases such as cardiac hypertrophy, ischemic/reperfusion injury associated with organ transplantation, and other surgical procedures such as percutaneous transluminal coronary angioplasty (PTCA).

Due to their Na/H exchange inhibiting properties, the acyl guanidine compounds can also be used for CNS disorders associated with cerebral ischemia such as cerebral infarction, cerebral edema and like. Additionally, they can be used for ischemia and ischemia-reperfusion injury resulting from shock and trauma.

The acyl guanidine compounds are also antithrombotic agents and antiproliferative agents and are also useful in treating renal disease.

The acyl guanidine compounds are also dual inhibitors of NHE-1 and NHE-3 and thus can be used as cardioprotectants for the treatment of heart disease, whilst also improving renal function by protecting against renal damage, or reversing hypertension by a direct modulation of sodium resorbtion in the kidney. As dual inhibitors, the compounds of the invention are also useful in a combination of therapies, for example, hypertension in patients with acute coronary syndromes, MI, recovery from MI and chronic stable angina. They are also useful for heart failure when an anti-hypertensive or diuretic agent is required for treatment.

Acyl guanidine compounds can be additionally used for the treatment of diabetes mellitus and other diabetic complications and for lowering serum lipids such as lowering LDL-cholesterol.

The acyl guanidine compounds can also be formulated in combination with a diuretic such as chlorothiazide, hydrochlorothiazide, flumethiazide, hydroflumethiazide, bendroflumethiazide, methylchlorthiazide, trichloromethiazide, polythiazide or benzthiazide as well as ethacrynic acid tricrynafen, chlorthalidone, furosemide, musolimine, bumetanide, triamterene, amiloride and spironolactone and salts of such compounds, angiotensin converting enzyme inhibitors such as captopril, zofenopril, fosinopril, enalapril, ceranopril, cilazopril, delapril, pentopril, quinapril, ramipril, lisinopril, and salts of such compounds, thrombolytic agents such as tissue plasminogen activator (tPA), recombinant tPA, streptokinase, urokinase, prourokinase, and anisoylated plasminogen streptokinase activator complex (APSAC, Eminase, Beecham Laboratories), or calcium channel blocking agents such as verapamil, nifedipine or diltiazem. Such combination products if formulated as a fixed dose employ the acyl guanidine compounds within the dose range described above and the other pharmaceutically active agent within its approved dose range.

The acyl guanidine compounds, and combinations thereof, can be formulated, as described above, in compositions such as tablets, capsules or elixirs for oral administration, in sterile solutions or suspensions for parenteral administration, and may also be administered via transdermal patch or nasal inhalation solutions. About 10 to about 500 milligrams of a compound of formula 9 is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The following examples and preparations describe the manner and process of making and using the invention and are of preferred embodiments of the invention. It should be understood that there may be other embodiments which fall within the spirit and scope of the invention as defined by the claims appended hereto.

EXAMPLE 1

4-Vinyl-2,3-dihydrobenzofuran

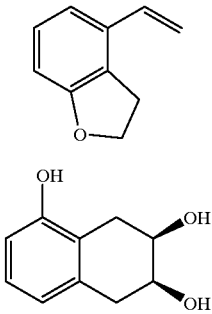

A.

3a-9a-cis-3a,4,9,9a-Tetrahydro-2,2-dimethyl-2H-naphtho[2,3-d]-1,3-dioxol-5-ol (described in J. Med. Chem., 1978, 21, 913) (200 g, 0.908 mole), methanol (500 ml), and distilled water (170 mL) were charged in a 1000 mL three-neck round bottom flask equipped with a mechanical stirrer, a reflux condenser, and a digital thermometer probe at room temperature to obtain a suspension. Trifluoroacetic acid (15 mL) was added to the suspension with stirring. The suspension was heated to reflux at 62.5° C. for 3 hr. The reaction mixture was cooled to ambient temperature. A white suspension appeared. Methanol and trifluoroacetic acid were removed under reduced pressure. Water (360 mL) was added to the suspension with stirring. The suspension was then heated to 90° C. to dissolve the precipitate. The mixture was stirred for 30 min at 90° C. and allowed to cool to ambient temperature over 30 min and set aside at ambient temperature for 16 hr. The resulting crystals were filtered and washed with cold distilled water (100 mL). The crystals were dried in vacuo at room temperature overnight to give 155.9 g of the desired triol (95.3% yield) as gray needles.

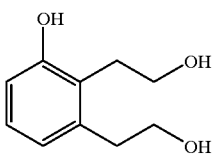

B.

Part A triol (140 g, 777 mmol), tetrahydrofuran (330 mL) and distilled water (660 mL) were charged to a 2000 mL three-neck round bottom flask equipped with a mechanical stirrer and a digital thermometer at ambient temperature. A suspension was formed. The suspension was cooled to 0° C. by using an ice-water bath. Sodium periodate (179.47 g, 839 mmol) was added portionwise (~10 g each) over a period of 80 minutes. The reaction mixture was stirred for additional 40 minutes at 0° C. The precipitate was filtered and washed with ethanol (2×125 mL). The filtrate and the ethanol solutions were combined and saved.

Absolute ethanol (700 mL) in a 3000 mL three-neck round bottom flask equipped with a mechanical stirrer, a digital thermometer, and a pressure equalizing addition funnel was cooled to −6° C. by using a dry-ice acetone bath. Sodium borohydride (88.18 g, 2.331 mol) was added and the resulting suspension was stirred for 5 min at −6° C. To this was added the dialdehyde solution (1200 mL) in ethanol (from above) dropwise over a period of 80 minutes with the temperature maintained between −3 and 0° C. The mixture was stirred for additional 40 minutes at 0° C. Acetone (300 mL) was added dropwise to above solution over a period of 40 minutes and while keeping the temperature below 3° C. The reaction mixture was stirred for additional 0.5 hrs below 3° C. It was then warmed to room temperature and stirred for 30 minutes.

Saturated ammonium chloride solution (500 mL) was then added at room temperature and the white precipitate was filtered and wash with ethanol (2×100 mL). The filtrate and the ethanol solutions were combined and the organic solvent removed under reduced pressure. Solid ammonium chloride (50 g) was added to the residue and the residue extract with ethyl acetate (5×400 mL). The combined organic layers were washed with 2:1 mixture of water:saturated sodium hydrogensulfite (300 mL), 1:1 mixture of water:brine (300 mL), and brine (2×300 mL). The organic phase was dried over magnesium sulfate and filtered. The solvent was removed under reduced pressure to give 136.13 g of the desired compound in 94.8% yield.

C.

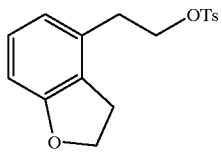

Part B triol (134 g, 735 mmol), pyridine (250 mL), and dichloromethane (350 mL) were charged in a 2000 mL three-neck round bottom flask equipped with a mechanical stirrer, a digital thermometer, and a pressure equalizing addition funnel at room temperature. The mixture was cooled to −40° C. by a dry-ice acetone bath. To this was added a solution of tosyl chloride (274.78 g, 1.442 mol) in pyridine (70 mL) and dichloromethane (400 mL) over a period of 170 minutes at −40° C. with good stirring. The mixture was stirred for an additional 3.5 hr at −35° C. Additional tosyl chloride (16.81 g, 88.2 mmol) was then added to the reaction mixture at −40° C. and the reaction mixture stirred for 30 minutes. The reaction mixture was warmed to −10° C. and dichloromethane (1500 mL) was added at −10° C. The reaction mixture was warmed to room temperature, washed with 2N HCl (4×650 mL), saturated NaHCO₃ (650 mL), brine (650 mL), dry over Na₂SO₄, and filtered. Solvent was removed under reduced pressure to give 360 g of crude ditosylate as a light yellowish residue which was used for the next step without any purification.

The crude ditosylate and methanol (2000 mL) were charged in a 3000 mL three-neck round bottom flask equipped with a mechanical stirrer, a digital thermometer, and a pressure equalizing addition funnel. The mixture was cooled to 0° C. by an ice-water bath. Anhydrous potassium carbonate (111.74 g, 809 mmol) was added portionwise to the methanol solution at 0° C. and the reaction mixture stirred at 0° C. for 2 hr. The reaction mixture was warmed to room temperature and stirred for additional 2 hr. The white precipitate was filtered and washed with ethyl acetate (2×100 mL). The filtrates were combined and concentrated to ~500 mL. The resulting precipitate was filtered and washed with 1:1 methanol:water (100 mL). The residue was dried in vacuum (~1 mmHg) for 3.5 hrs and over house vacuum overnight to give the desired compound (197.0 g, 84% yield).

D.

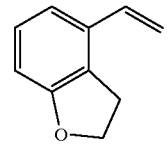

The Part C tosylate (100 g, 314 mmol) was dissolved in THF (1200 mL) in a 2000 mL three-neck round bottomed flask equipped with a mechanical stirrer, a digital thermometer, and a pressure equalizing addition funnel at room temperature. The reaction mixture was cooled to 0° C. by an ice-water bath. To this was added a solution of t-BuOK (1 M, 345.5 mL) in THF dropwise at 0° C. over a period of 110 min. The reaction mixture was warmed to ambient temperature and stirred for additional 2 hr. Water (350 mL) and EtOAc (600 mL) were added and the two layers were separated. The aqueous layer was further extracted with EtOAc (2×150 mL). The combined EtOAc layers were washed with brine (2×150 mL) dried over MgSO₄ and filtered. The solvent was removed under reduced pressure to give 46 g of the title styrene in 100% yield.

EXAMPLE 2

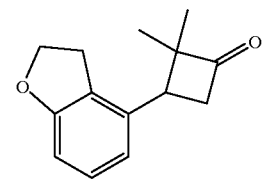

To a flame-dried 1L three necked round bottom flask equipped with a magnetic stirrer was added N,N, 2-trimethyl propionamide (17.8 mL, 0.138 mol) and anhydrous methylene chloride (200 mL). The mixture was stirred to give a solution under argon and cooled to −15° C. Trifluoromethanesulfonic anhydride (26 mL, 0.154 mol) was added via syringe and the resulting mixture was stirred at −15° C. for 10 minutes. A solution of

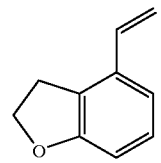

(from Example 1) (17.5 g, 0.12 mol), and collidine (21 mL, 0.155 mol) in anhydrous methylene chloride (30 mL) was added at −15° C. After the addition was completed, the reaction mixture was heated to reflux and stirred for 20 hours. The solvent was removed on a rotary evaporator and the residue oil was washed with ether (3×100 mL). The residue which contains 2,2-dimethyl-3-(2',3'-dihydrobenzofuran-4'-yl)cyclobutanone iminium salt

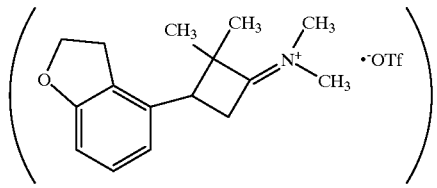

was then dissolved in methylene chloride (150 mL). Water (150 mL) was added and the mixture was refluxed for 6 hours. After cooling to room temperature, the phases were separated. The aqueous layer was extracted with methylene chloride (2×100 mL). The rich organic layers were combined, washed with brine (200 mL) and dried over anhydrous sodium sulfate. After removal of sodium sulfate by filtration, the filtrate was concentrated to give an oil which was purified by silica gel chromatography using 5–10% EtOAc/hexane as the eluent to give 19.0 g (73%) title compound as a white crystalline compound. HPLC, 100A % at 220 nm.

$^1$H NMR (CDCl$_3$) d, 7.14 (t, J=7.8 Hz, 1H), 6.72 (t, J=8.2 Hz, 2H), 4.52–4.65 (m, 2H), 3.50 (dd, J=7.0, 16.4 Hz, 1H), 3.08–3.41 (m, 4H), 1.38 (s, 3H), 0.83 (s, 3H).

EXAMPLE 3

3,3-Dimethyl-2-(2',3'-dihydrobenzofuran-4'-yl) cyclopropane carboxylic acid

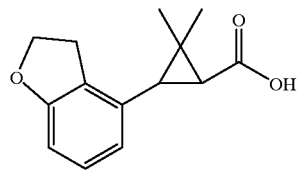

To an oven dried 3L three necked round bottom flask equipped with a mechanical stirrer was placed Example 2 compound (20.0 g, 92.47 mmol) and anhydrous THF (925 mL). The mixture was stirred to give solution and cooled to −65° C. A solution of 1N LiHMDS in THF (101.7 mL, 101.7 mmol) was added over 15 minutes while keeping the pot temperature below −55° C. The resulting mixture was stirred at −70° C. for 30 minutes and 0° C. for 15 minutes. After cooling back to −70° C., a solution of N-bromosuccinimide (NBS) (16.4 g, 92.2 mmol) in anhydrous THF (230 mL) was added over 5 minutes. After addition was completed the cooling bath was replaced with an ice-water bath and the reaction mixture was stirred to 0° C. for 10–20 minutes at which time HPLC indicated that the bromination was complete. A solution of sodium hydroxide (23.1 g, 577.5 mmol) in DI water (230 mL) was added at 0° C. and the resulting reaction mixture was stirred at room temperature for 15–30 minutes at which time the ring contraction reaction was complete. THF was removed on a rotary evaporator and the rich aqueous was washed with MTBE (2×125 mL). The residual organic solvent was removed on rotary evaporator and the rich aqueous was diluted with DI water (250 mL). The pH of the resulting rich aqueous was then adjusted from ~12.5 to 1.0 using conc. HCl (47 mL). The resulting slurry was cooled to 0° C. and stirred for 30 minutes. The slurry was filtered, washed with ice-cold DI water (3×50 mL) and suction dried for 18 hours to give 20.6 g (96%) of title compound as white crystalline compound. HPLC 97.7A % at 220 nm.

$^1$H NMR (CDCl$_3$) d 7.07 (t, J=7.8 Hz, 1H), 6.71 (d, J=7.9 Hz, 1H), 6.59 (d, J=7.6 Hz), 4.61 (t, J=8.9 Hz, 2H), 2.23–3.32 (m, 1H), 3.07–3.15 (m, 1H), 2.61 (d, J=5.9 Hz, 1H), 2.00 (d, J=5.9 Hz, 1H), 1.47 (s, 3H), 1.00 (s, 3H). $^{13}$C NMR (CDCl$_3$) d 179.3, 160.2, 134.4, 128.4, 127.5, 120.1, 108.3, 71.5, 37.1, 31.6, 30.8, 29.3, 22.4, 20.9.

EXAMPLE 4

Resolution of Example 3 Acid

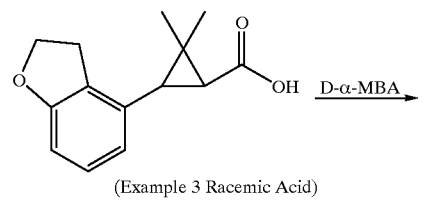

(Example 3 Racemic Acid)

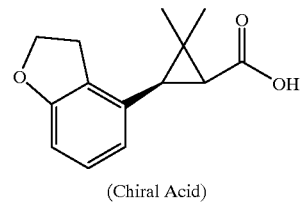

(Chiral Acid)

(1S,2S)-3,3-Dimethyl-2-(2',3'-dihydrobenzofuran-4'-yl)cyclopropane carboxylic acid/(R)-1-phenylethylamine salt To a stirring solution of Example 3 acid (14.0 g, 60.27 mmols) in absolute ethanol (420 mL) at 55° C. was added (R)-1-phenylethylamine (9.2 mL, 72.33 mmols) in one portion. To the solution was added a seed crystal then the mixture was allowed to slowly cool to room temperature with stirring over 2 hrs, then the mixture was stirred an additional 18 hrs at room temperature. The solid was isolated by filtration, washed with hexanes (3×5 pad volumes), air-dried (30 min), dried under vaccum (<2 mm Hg, 16 hr) to afford 7.89 g of amine salt as a white powder (37% yield; 50% theoretical maximum).

$^1$H NMR (270 MHz, CDCl$_3$ with CD$_3$OD): δ 7.20–7.50 (m, 5H), 7.02 (dd, J=7.9 and 7.7 Hz, 1H), 6.65 (d, J=7.9 Hz, 1H), 6.58 (d, J=7.7 Hz, 1H), 4.58 (dd, J=9 and 9 Hz, 2H), 4.24 (q, J=6.7 Hz, 1H), 3.0–3.4 (m, 2H), 2.42 (d, J=5.9 Hz, 1H), 1.92 (d, J=5.9 Hz, 1H), 1.54 (d, J=6.7 Hz, 1H), 1.39 (s, 3H), and 0.92 (s, 3H).

EXAMPLE 5

(1S,2S)-3,3-Dimethyl-2-(2',3'-dihydrobenzofuran-4'-yl)cyclopropane carboxylic acid

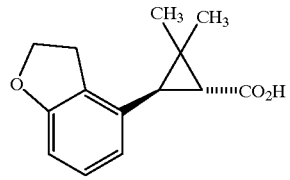

To a suspension of Example 4 amine salt (3.70 g, 10.47 mmol) in EtOAc (50 mL) was added 1N HCl (25 mL) at room temperature. After mixing vigorously, the aqueous solution was removed. The organic solution was washed with sat. aq. NaCl (25 mL), dried (anhyd. MgSO₄), filtered, and concentrated in vacuo to afford 2.42 g of chiral acid as a white solid (99% yield).

1H NMR (270 MHz, CDCl₃): δ 7.05 (dd, J=7.9 and 7.7 Hz, 1H), 6.68 (d, J=7.9 Hz, 1H), 6.58 (d, J=7.7 Hz, 1H), 4.59 (dd, J=9 and 9 Hz, 2H), 2.9–3.4 (m, 2H), 2.59 (d, J=5.9 Hz, 1H), 1.98 (d, J=5.9 Hz, 1H), 1.45 (s, 3H), and 0.98 (s, 3H).

EXAMPLE 6

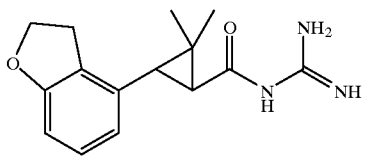

To a stirring solution of Example 5 chiral carboxylic acid (12 g, 51.7 mmol) in anhydrous DMF (70 mL) was added CDI (10.05 g, 62.04 mmol) in small portions. After 2 h. under argon at RT, a solution of free base guanidine (6.1 g, 103.4 mmol) in DMF (20 mL) was added. Stirring was continued for 18 h at RT. The reaction mixture was diluted with ethyl acetate and washed with water (×5); followed by brine (×1); dried over MgSO₄; filtered and solvent was removed in vacuo, affording the crude product as a white foam. The crude product was subjected to reversed phase preparative HPLC (C18 column/water-MeOH-TFA 80:20:0.1 to 10:90:0.1 gradient) to afford a TFA salt of the title compound. This was dissolved in EtOAc, adjusted to pH 7–8 with saturated Na₂CO₃ aqueous solution, diluted with water, the organic layer was died over MgSO₄; filtered and concentrated in vacuo, affording the title compound as a free base. This was taken in THF and treated with 14 mL 4N HCl in dioxane at 0° C. with swirling. The solvent was removed in vacuo and the residue was lyophilized from water to afford the title compound as the HCl salt (white solid, 8.6 g, 54% yield).

MS m/e (M+H)+274+; ¹H NMR (270 MHz; CDCl₃) d 11.8 (s, 1H); 8.4 (bs, 4H); 7.26 (s, CHCl3); 7.01 (t, J=7.84, 1H); 6.67 (d, J=7.94, 1H); 6.55 (d, J=7.65, 1H); 4.58(t, J=9.2, 2H); 3.25 (m, 1H); 5.05(m, 1H); 2.71(d, J=5.6, 1H); 2.12 (d, J=5.7, 1H); 1.4 (s, 3H); 0.99 (s, 3H).

¹³C NMR (270 MHz; CDCl₃) 20.52, 22.21, 29.29, 33.22, 34.47, 37.46, 71.43, 77.1, 77.42, 77.75, 108.6, 119.9, 127.4, 128.5, 133.5, 156.4, 160.3, 173.9. Optical rotation [a]$_D$+7.3° c=1 CHCl₃.

Elemental Analysis: $C_{15}H_{19}N_3O \cdot 1.0\ HCl \cdot 0.806H_2O$

|  | % C | % H | % N |
|---|---|---|---|
| Calculated: | 55.55 | 6.72 | 12.96 |
| Found: | 55.55 | 6.43 | 13.03 |

What is claimed is:

1. A process for preparing a chiral cyclopropane carboxylic acid of the structure

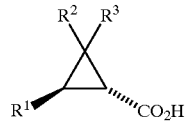

wherein $R^1$ is aryl or heteroaryl and $R^2$ and $R^3$ are the same or different and are each lower alkyl, or $R^2$ and $R^3$ taken together with the carbon to which they are attached form a 3 to 7 membered carbocyclic ring, which comprises providing an alkylidene compound of the structure

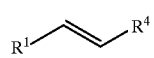

wherein $R^4$ is H or lower alkyl, reacting the alkylidene compound with an N,N-disubstituted ketene iminium salt of the structure

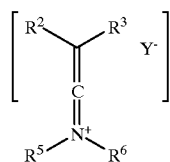

wherein $R^5$ and $R^6$ are the same or different and are each lower alkyl, and

Y is trifluoromethanesulfonate (OTf), to form a cyclobutane iminium salt of the structure

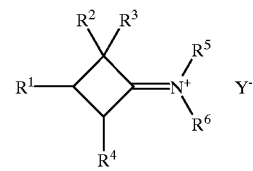

hydrolyzing the cyclobutane iminium salt to form a cyclobutanone of the structure

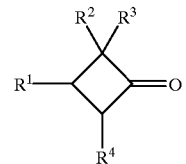

treating the cyclobutanone with a base to form an enolate, and then reacting the enolate with a halogenating agent to form an α-halocyclobutanone of the structure

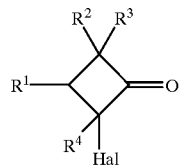

where Hal is Cl, Br, F or I, treating the α-halocyclobutanone with a base to form a cyclopropane carboxylic acid of the structure

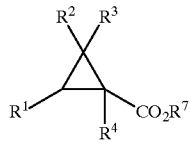

wherein $R^7$ is H or lower alkyl, reacting the cyclopropane carboxylic acid with a chiral amine of the structure

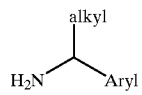

to form the cyclopropane carboxylic acid amine salt of the structure

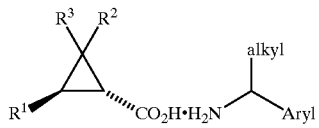

and treating the cyclopropane carboxylic acid amine salt with aqueous acid to form the cyclopropane carboxylic acid of the structure

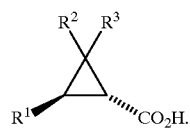

2. The process as defined in claim 1 wherein $R^1$ is heteroaryl.

3. The process as defined in claim 1 wherein $R^1$ is

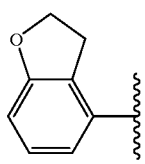

and $R^2$ and $R^3$ are each $CH_3$.

4. A process for preparing a cyclopropane carboxylic acid of the structure

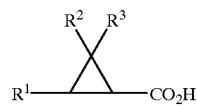

wherein $R^1$ is aryl or heteroaryl, and $R^2$ and $R^3$ are the same or different and are each lower alkyl or $R^2$ and $R^3$ together with the carbon to which they are attached form a 3 to 7 member carbocyclic ring, which comprises providing an α-haloketone of the structure

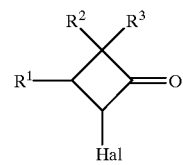

wherein the α-haloketone is prepared via the steps of reacting a cyclobutanone of the structure

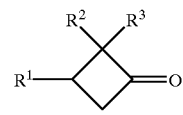

with a base to form an enolate, reacting the enolate with a halogenating agent to form the corresponding α-haloketone,

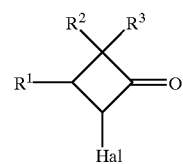

and reacting the α-haloketone with a base to form the cyclopropane carboxylic acid.

5. The process as defined in claim 4 wherein $R^1$ is

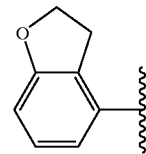

and $R^2$ and $R^3$ are each $CH_3$.

6. A process for preparing a cyclopropane carboxylic acid of the structure

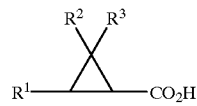

wherein $R^1$ is aryl or heteroaryl, and $R^2$ and $R^3$ are the same or different and are each lower alkyl, or $R^2$ and $R^3$ together with the carbon to which they are attached form a 3 to 7 member carbocyclic ring, which comprises providing a cyclobutanone iminium salt of the structure

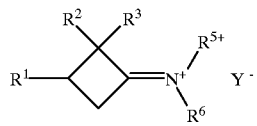

wherein $R^5$ and $R^6$ are the same or different and are each lower alkyl, and Y is trifluoromethanesulfonate, hydrolyzing the cyclobutanone iminium salt to form a cyclobutanone of the structure

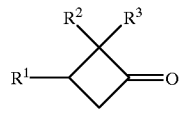

treating the cyclobutanone with a base to form an enolate, and then reacting the enolate with a halogenating agent to form an α-halocyclobutanone of the structure

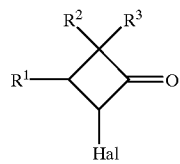

where Hal is Cl, Br, F or I, and treating the α-halocyclobutanone with a base to form the cyclopropane carboxylic acid or an ester thereof.

7. The process as defined in claim 6 wherein $R^1$ is

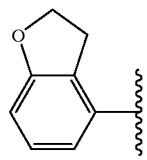

and $R^2$ and $R^3$ are each $CH_3$.

8. The process as defined in claim 7 wherein the cyclobutanone iminium salt is prepared via the steps of providing an alkylidene compound of the structure

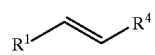

wherein $R^4$ is hydrogen;

reacting the alkylidene compound with an N,N-disubstituted ketene iminium salt of the structure

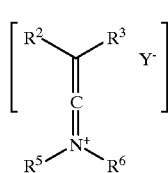

wherein $R^5$ and $R^6$ are the same or different and are each lower alkyl, and Y is OTf, to form the cyclopropane iminium salt of the structure

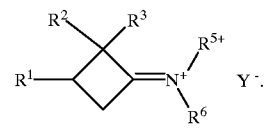

9. The process as defined in claim 8 wherein $R^1$ is

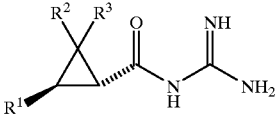

and $R^2$ and $R^3$ are each $CH_3$.

10. A process for preparing an acyl guanidine of the structure

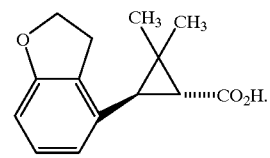

wherein $R^1$ is aryl or heteroaryl, and $R^2$ and $R^3$ are the same or different and are each lower alkyl, or $R^2$ and $R^3$ together with the carbon to which they are attached form a 3 to 7 member carbocyclic ring, which comprises providing a chiral cyclopropane carboxylic acid of the structure and converting the chiral cyclopropane carboxylic acid to the acyl guanide.

11. The process as defined in claim 10 wherein the chiral cyclopropane carboxylic acid is converted to the acyl guanide by reacting the chiral acid with guanidine in the presence of a coupling agent.

12. The process as defined in claim 10 wherein the chiral cyclopropane carboxylic acid is

13. A process for preparing a chiral form of 2-(2',3'-dihydrobenzofuran-4'-yl)cyclopropane carboxylic acid of the structure

[trans structure: 2,3-dihydrobenzofuran-4-yl cyclopropane with gem-dimethyl and CO₂H]

which comprises (a) providing a 2-(2',3'-dihydrobenzofuran-4'-yl) cyclopropane carboxylic acid of the structure

[structure with CO₂R⁷]

wherein R⁷ is H or lower alkyl, (b) if R⁷ is lower alkyl, hydrolyzing the ester to the corresponding acid,
(c) reacting the acid with a chiral amine of the structure

[H₂N-CH(alkyl)(Aryl)]

to form an amine salt of the structure

[amine salt structure CO₂H·H₂N-CH(alkyl)(Aryl)]

and (d) reacting the amine salt with aqueous acid to form the chiral acid of the structure

[chiral acid structure with CO₂H]

or alternatively, if in

[structure with CO₂R⁷]

R⁷ is lower alkyl, subjecting the above ester to enzymatic hydrolysis to form the chiral acid of the structure

[chiral acid structure with CO₂H]

14. A compound of the structure $$R^1\text{———}CO_2H \; ; \; or \; R^1\text{———}CO_2H \; ; \; or$$

$$R^1\text{———}=O \; or \; R^1\text{———}=O \; ;$$
                                          Hal $$R^1\text{———}N^+\begin{matrix}R^5\\R^6\end{matrix} \; Y^- \; ; \; or$$

[cyclopropane structure with CO₂H·H₂N-CH(alkyl)(Aryl)]

where R¹ = [2,3-dihydrobenzofuran-4-yl]

where R¹=

R⁵ is lower alkyl,
R⁶ is lower alkyl, and
Y is OTf.

15. A process for preparing an acyl guanidine of the structure

[acyl guanidine structure with dihydrobenzofuran, gem-dimethyl cyclopropane, C(O)NH-C(=NH)NH₂]

providing an alkylidene compound of the structure

[2,3-dihydrobenzofuran-4-yl vinyl]

reacting the alkylidene compound with an N,N-disubstituted ketene iminium salt of the structure

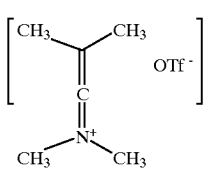

to form a cyclobutanone iminium salt to the structure

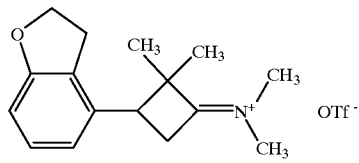

hydrolyzing the cyclobutanone iminium salt to form a cyclobutanone of the structure

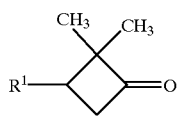

treating the cyclobutanone with a base and then a halogenating agent to form an α-halocyclobutanone of the structure

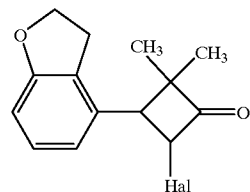

wherein Hal is Cl, Br, F or I, treating the α-halocyclobutanone with a base to form a cyclopropane carboxylic acid of the structure

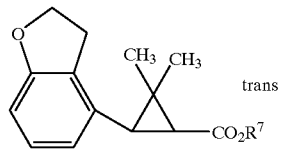

wherein $R^7$ is H or lower alkyl,
  (a) if $R^7$ is a lower alkyl, hydrolyzing the ester to the corresponding acid (b) reacting the acid with a chiral amine of the structure

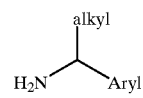

to form an amine salt of the structure

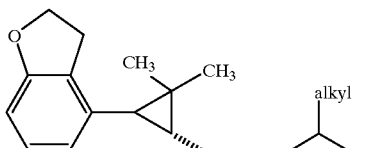

and
  (d) reacting the amine salt with aqueous acid to form the chiral acid of the structure

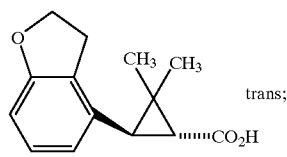

or alternatively, if in

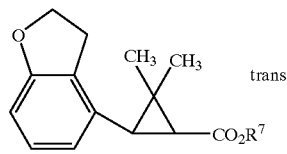

$R^7$ is lower alkyl, subjecting the above ester to enzymatic hydrolysis to form the chiral acid of the structure

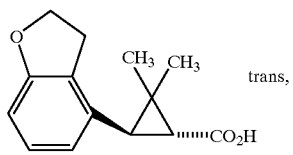

and reacting the chiral cyclopropane carboxylic acid with guanidine in the presence of a coupling agent.

* * * * *